United States Patent [19]

Lai et al.

[11] 4,298,737

[45] Nov. 3, 1981

[54] PIPERDINYL SUBSTITUTED 1,4-DIAZA-2-CYCLOALKANONES AND DERIVATIVES THEREOF

[75] Inventors: John T. Lai, Broadview Heights; Pyong-Nae Son, Akron, both of Ohio

[73] Assignee: The B. F. Goodrich Company, Akron, Ohio

[21] Appl. No.: 87,264

[22] Filed: Oct. 22, 1979

Related U.S. Application Data

[62] Division of Ser. No. 972,834, Dec. 26, 1978, abandoned.

[51] Int. Cl.$^3$ ............................................. C07D 241/04
[52] U.S. Cl. .............................. 544/360; 260/239 BC; 544/359
[58] Field of Search ............................... 544/360, 359; 260/239 BC

[56] References Cited

U.S. PATENT DOCUMENTS

| | | | |
|---|---|---|---|
| 3,311,624 | 3/1967 | Ohnacker et al. | 544/360 |
| 4,190,571 | 2/1980 | Lai et al. | 544/360 |

*Primary Examiner*—Nicholas S. Rizzo
*Attorney, Agent, or Firm*—John H. Faro

[57] ABSTRACT

Improved process for the synthesis of piperidinyl substituted 1,4-diaza-2-cycloalkanones and substituted derivatives thereof, involving solid-liquid phase transfer phenomena. More specifically, the subject compounds are prepared by combining a piperidinyl substituted diamine and a suitable coreactant in the presence of a phase transfer catalyst and caustic. Compounds prepared in this fashion are suitable as UV stabilizers for photodegradable plastics.

6 Claims, No Drawings

PIPERDINYL SUBSTITUTED 1,4-DIAZA-2-CYCLOALKANONES AND DERIVATIVES THEREOF

This is a division of application Ser. No. 972,834, filed Dec. 26, 1978, now abandoned.

BACKGROUND OF THE INVENTION

1. Field of the Invention

This invention relates to a process and novel compounds prepared thereby. More specifically, this invention is directed to the synthesis of piperidinyl substituted, 1,4-diaza-2-cycloalkanones by a technique involving solid-liquid phase transfer phenomena.

2. Description of the Prior Art

The increasing use of polymers in place of the more traditional types of structural materials (e.g. wood, metals, etc.) has necessitated the compounding of such polymers with a variety of stabilizers in order to enhance the ability of such polymers to withstand prolonged exposure to a variety of degradative forces. Degradation of such environmentally sensitive polymers can be caused by exposure to light, heat and/or air. Such degradation is usually manifest by either a partial or total loss of structural integrity, changes in light transmission properties, changes in color, loss or reduction in flexibility and/or resiliency, or any combination of the above phenomenon. As will be appreciated, the stabilizers which are used in conjunction with the above polymeric materials, in addition to providing protection against such degradative changes, must also be compatible with the aesthetic properties of the polymeric article and be effective at low concentrations. The economics of the marketplace dictate that these stabilizers be relatively inexpensive and capable of preparation from readily available starting materials by simple and straightforward synthesis techniques.

The diazacycloalkanones have been found to be highly effective in the stabilization of polymeric materials against the photodegradative forces of ultraviolet light. The efficacy of such materials in the UV stabilization of polymers is described in copending patent applications Ser. Nos. 835,065 now U.S. Pat. No. 4,190,571 and 835,069, now U.S. Pat. No. 4,207,228 both filed on Sept. 21, 1977; the Ser. No. 835,065 application entitled "Substituted 2-keto-1,4-Diaza Cycloalkanes and UV Light Stabilized Compositions Containing Same" and the Ser. No. 835,069 application entitled "UV Light Stabilized Compositions Containing Substituted 1,5-diazacycloalkanes and Novel Compounds". The aforementioned applications disclose methods for the preparation of compounds useful in the stabilization of UV sensitive polymer compositions. A third copending application entitled "Synthesis of 2-keto-1,4-Diazacycloalkanes" (Ser. No. 835,066 also filed Sept. 21, 1977) discloses a variety of techniques for the convenient synthesis of highly effective UV stabilizer compounds. The principal advantages of the synthesis described in the Ser. No. 835,066 application reside in the utilization of readily available starting materials, the utilization of conventional processing apparatus, the absence of hydrogen cyanide and the attendant hazards associated therewith.

In copending application Ser. No. 835,066, in the section entitled "Background of the Invention", certain references are enumerated which disclose cycloalkanes as useful UV stabilizers—see for example OLS No. 2,315,042; JAP Pat. Nos. 74-53,571 and 74-53,572; and U.S. Pat. Nos. 3,919,234; 3,920,659 and 3,928,330. Also discussed in this same section are structurally similar compounds and the limitations on the synthesis of such compounds and the analogs thereof. To the extent that this discussion is relevant to subject matter of the invention described and claimed hereinafter, it is hereby incorporated by reference in its entirety.

The prior art also discloses separate reaction of primary and secondary amines with chloroform in the presence of a phase transfer catalyst and caustic. The resultant product obtained thereby (in the case of the primary amine) was an isonitrile derivative of the primary amine; and (in the case of the secondary amine) was a foramide derivative of the secondary amine. See W. P. Weber et al, Tel.Lett 1637(1972) and J. Graefe, et al Z.Chem. 434(1974) or M. Makosza et al Rocz.Chem. 49,1627(1915) respectively. Presumably, were one to react both primary and secondary amines with chloroform under essentially the same conditions, a mixture of products would be obtained although the above references do not address this possibility.

The preparation of UV stabilizers by reaction of an appropriately substituted diamine and a suitable co-reactant in the presence of a phase transfer catalyst and caustic is the subject of copending patent application, Ser. No. 916,640, filed June 19, 1978, now U.S. Pat. No. 4,167,512 in the name of John TaYuan Lai entitled, "Synthesis of 2-Keto-1,4-Diazacycloalkanes". The diamines suitable for use in such synthesis can include both primary and secondary amines. Such amines can have pendant from their $\alpha$-carbons an alkyl, aryl and/or heterocyclic substituent. The provision of a specific example in the above-referenced copending application of such a heterycyclic substituted diamine is lacking.

In summary, the processes discussed in the "Background of the Invention" section of the above referenced copending application, Ser. No. 835,066 do not provide convenient techniques for the preparation of poly-substituted, 1,4-diaza-cycloalkanones. The well-known reaction of primary and secondary amines with chloroform in the presence of a phase transfer catalyst and caustic are reportedly directive for the synthesis of an isonitrile derivative of the primary amine and a form-amide derivative of the secondary, respectively. The disclosure by J. T. Lai in his previously referenced copending Ser. No. 916,640 of the formation of 1,4-diaza-cycloalkanones by reaction of chloroform and "mixed" primary and secondary amines in the presence of phase transfer catalyst and caustic is thus quite unexpected. Additional effort is, however, required to realize the full scope of his discovery with respect to the synthesis of compounds have substantial stabilizer properties.

SUMMARY OF THE INVENTION

Accordingly, it is the object of this invention to remedy the above as well as related deficiencies in the prior art.

More specifically, it is the principal object of this invention to provide a process for the synthesis of substituted 1,4-diazacycloalkanones.

It is another object of this invention to provide a process for the preparation of piperidinyl substituted, 1,4-diaza-2-cycloalkanones.

Additional objects of this invention include utilizing the compounds prepared thereby in the stabilization of photo-degradable polymers.

The above and related objects are achieved by contacting an N-piperidinyl substituted diamine with a coreactant in the presence of a phase transfer catalyst and caustic. In one of the preferred embodiments of this invention, the exotherm of the reaction is controlled by chilling of the reaction vessel. In another of the preferred embodiments of this invention, the reactants and catalysts are contacted with one another while dispersed in a nonpolar organic solvent, such as dichloromethane.

DESCRIPTION OF THE INVENTION INCLUDING PREFERRED EMBODIMENTS

In a typical embodiment of the process of this invention, an appropriately substituted diamine and a coreactant, such as α-trichloroalkyl alcohol; a mixture of α-cyanoalkyl alcohol and a haloform; or a mixture of an aliphatic ketone and a haloform, in the desired relative concentrations, are introduced into a reaction vessel followed thereafter by the addition to said vessel of a phase transformation catalyst dissolved in a nonpolar organic solvent. To this reaction mass is thereafter added caustic (either solid or liquid). The reaction vessel is preferably at least partially immersed in an ice bath to control the exotherm of the reaction. The presence of the caustic in the reaction medium also serves a similar function, that is, it retards the rate of reaction and thus the heat generated during the combination of the reactants is significantly reduced.

The ratio of reactants to one another in this process is not believed to be critical to the formation of the desired product. However, where one desires to obtain high yields and ease of separation of the reaction product from the various reactants and catalysts used in such preparation, it is preferable to adjust the relative mole concentration of materials so that the ratio of N-piperidinyl substituted diamine to co-reactant is in a range of from about 0.5:1 to about 1:1.

As the result of the interaction of the above materials in the reaction vessel, a water-soluble solid is formed. This solid can be removed from the nonpolar reaction medium by filtration or by the addition of water to the reaction medium followed thereafter by separation of the aqueous from the organic fluid phase. The aqueous phase is thereafter further extracted with an organic solvent such as chloroform and the combined organic solutions washed with water, dried over sodium sulphate and concentrated. The desired product is crystallized or distilled from the combined organic solutions and recrystallized in the conventional manner to yield a relatively pure product.

The N-piperidinyl substituted diamines suitable for use in this process have the following structural formula:

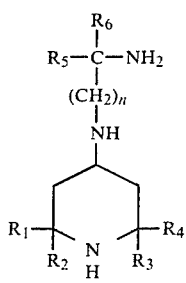

I wherein $R_1$ through $R_4$ can be hydrogen or alkyl of 1 to 10 carbon atoms;

$R_5$ and $R_6$ are independently selected from the group consisting of alkyl of 1 to 12 carbon atoms, cycloalkyl, hydroxycycloalkyl, aminoalkyl, alkenyl, aralkyl and alkylene, provided further that any two of said substituents pendant from the same carbon atom can collectively form a cyclic or alicyclic hydrocarbon; and n is 1 to 3.

A preferred compound within the scope of the above structural formula suitable for use in the process of this invention is 4-(3-amino-1,3-dimethyl-butylamino)-2,2,6,6-tetramethylpiperidine.

The coreactants which are suitable for use in the process of this invention can include α-trihaloalkyl alcohols, mixtures of a haloform and an α-cyanoalkyl alcohols, and/or mixtures of a haloform and an aliphatic ketones. The trihaloalkylalcohol which is suitable for use in the process of this invention can be represented by the following formula:

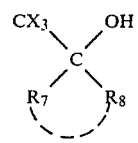

II wherein $R_7$ and $R_8$ are selected from the same group of substituents as $R_5$ through $R_6$ above; and X is halogen.

In the preferred embodiments of the process of this invention, the α-trihaloalkyl alcohol is symmetrically substituted at the β carbon. One such material which is especially preferred for use in the process of this invention is 1,1,1-trichloro-2-methyl-2-propanol hydrate. The alcohols which are highly suitable for use in this process include α-trichloromethyl-2-propanol, α-trichloromethyl-cyclohexanol, and α-trichloromethyl-1-butanol.

The coreactant mixtures which are suitable for use in the process of this invention contain a haloform, (e.g. chloroform or bromoform) in addition to an α-cyanoalkylalcohol or an aliphatic ketone. The concentration of the haloform relative to the other component of the mixture can vary and is preferably present in stoichiometric amounts (in relation to the α-cyanoalkylalcohol, at a mole ratio of about 1:2 and, in relation to the aliphatic ketone, at a mole ratio of about 1:1) although a stoichiometric excess is most preferred.

The α-cyanoalkylalcohols which are suitable for use in this process can be represented by the following formula:

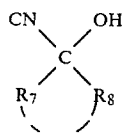

III wherein $R_7$ and $R_8$ are selected from the same group of substituents as $R_5$ through $R_6$ above.

The aliphatic ketones which are suitable for use in the process of this invention can be represented by the following formula:

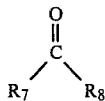

wherein $R_7$ and $R_8$ are selected from the same group of substituents as $R_5$ through $R_6$ above.

As indicated hereinabove, one or more of the above coreactants, and the haloform were required, are contacted with an N-piperidinyl substituted diamine in the presence of a "phase transfer catalyst". The phrase "phase transfer catalyst" is intended to describe, in the context of this invention, any compound which in the presence of the above reactants, causes a condensation of the coreactant and diamine in such a fashion so as to result in the formation of a cyclic ketone wherein the oxygen is doubly bonded to the α-carbon of the coreactant material. The phrase "phase transfer catalysts" is intended to describe, in the context of this invention, any compound, which in the presence of the above reactants, causes a condensation of the coreactants and the diamine in such a fashion so as to result in the formation of a cyclic ketone wherein the oxygen is doubly bonded to an α-carbon of the coreactant material.

Materials which have been found to effectively catalyze condensation of the diamine and coreactants in this fashion can be represented by the following formula:

wherein $Q^+$ is $NR_4$, $PR_4$ provided that
R is alkyl of 1–20 carbon atoms, aryl, aralkyl, or hydroxyalkyl; and
B is a mono-valent anion.

In addition to the above reactants and catalysts, a controlled amount of caustic is also employed in the process of this invention. The caustic may be present as a solid or as an aqueous solution and is added to the reaction mass, preferably subsequent to all reactants and catalysts. Concentration of caustic relative to the N-piperidinyl substituted diamine can vary and will ordinarily be present in the reaction mass in excessive stoichiometric quantities; preferably in the relative mole ratio of from about 3.3:1 to about 6:1. The addition of caustic to the reaction mass retards formation of the desired product and does thereby help control the exotherm of the reaction. The caustic is preferably added to the reaction mass in a solid form.

Stabilizer materials prepared according to the above processes, can be incorporated within ultraviolet light sensitive polymers by well-known techniques and by means of standard processing equipment. In order to most effectively achieve the desired level of stabilization, the dispersion of the stabilizer compound must be essentially uniform throughout the environmentally sensitive polymer. Ordinarily, the concentration of stabilizer in the polymer required to effect the requisite resistance to ultraviolet light degradation will range from about 0.5 to about 10 parts by weight stabilizer per 100 parts by weight ultraviolet light sensitive polymer. In the preferred embodiments of this invention, the concentration of stabilizer relative to environmentally sensitive polymer will rarely exceed 5 parts by weight per 100 parts by weight polymer, and is most preferably about 1 part by weight stabilizer per 100 parts by weight polymer. Virtually all polymeric materials are sensitive, at least to some degree, to photodegradation by ultraviolet light. The term "photodegradation" are used herein with reference to the ultraviolet light sensitive polymer materials is intended to be inclusive of any photo-induced change in physical, chemical and/or or electrical properties of the polymer or articles prepared therewith. Ultraviolet light sensitive polymers which are specially suitable for use in the compositions of this invention include any polymeric material which manifests such degradation upon exposure to UV irradiation. Such degradation of the polymer can manifest itself as discoloration and/or embrittlement.

The environmentally sensitive polymers which can be protected against photodegradation with the stabilizers described herein include PVC resins, ABS resins, polystyrene, polyacrylonitrile, polymethacrylate, polycarbonates, phenol-formaldehyde resins, polyepoxides, polyesters, polyolefins (especially homo and copolymers of polyethylene, polypropylene, ethylene-propylene copolymers, ethylene-vinyl acetate copolymers) and the like. In the preferred compositions of this invention, the ultraviolet light sensitive polymers which are stabilized as described herein are derived from α-monoolefin monomers such as ethylene, propylene, isobutylene, 1-butene, 1-pentene, 1-hexene, 4-methyl-1-pentene, and the like.

The stabilized polymer composition prepared as described herein, can contain in addition to the stabilized material described above, a variety of optional ingredients.

Such optional ingredients can include metal oxides, such as zinc, calcium and magnesium oxide; fatty acids such as stearic acid, lauric acid and salts thereof; fillers such as calcium and magnesium carbonate, calcium and barium sulfonates, aluminum silicates, asbestos, and the like; plasticizers and extenders, such as dialkyl and diaryl organic acids, i.e. diisobutyl, diisooctyl, and diisodecyl, and dibenzyl oleates, stearates, sebacates, azeolates, phthalates, and the like; ASTM II petroleum oils paraffinic oils, castor oil, tall oil, glycerin, and the like; antioxidants, such as 2,6-di-t-butyl paracresol, 2,2'-methylene-bis-(4-ethyl-6-t-butyl-phenol), 2,2'-,methylene-bis(6-t-butyl-4-methylphenol), 4,4-butylidene-bis-6-(t-butyl-n-cresol), 2-(4-hydroxy-3,5-di-t-anilino-4,5-bis(octylthio)-(1,3,5-triazine)hexahydro-1,3,5-tris-β-(3,5-di-t-butyl-4-hydroxylphenol)-propanyl-s-triazine, tris(3,5-di-t-butyl-4-hydroxybenzyl) isocyanurate, tetrakis[methylene-3-(3',5'-di-t-butyl-4'-hydroxyphenol)-propionate]methane, distearylthiodipropionate, dilaurylthiodipropionate, tri-(nonylphenyl)phosphite, tinthioglycolate, and the like; and other conventional ingredients, such as pigments, tackifiers, flame retardants, fungicides, and the like.

Other optional compounding ingredients which are especially useful in combination with the stabilizer compounds of this invention are the antioxidants. The inclusion within the composition of an antioxidant, in addition to the UV stabilizer confirms upon the polymer composition stability against two of more environmentally hostile degradative forces. The antioxidants which can be present within the polymer composition are generally used at concentrations in the range from about 0.1 to about 10 parts parts by weight per 100 parts by weight polymer, preferably, from about 0.2 to about 5 parts by weight per 100 parts by weight polymer. Generally, the phenolic antioxidants are preferred for use in conjunction with the UV stabilizers in the compositions of this invention.

The environmentally sensitive polymers which are stabilized in accord with the procedures described herein can be compounded with the various types of stabilizers and other additives cited hereinabove by standard mixing techniques and with standard equipment; such as in a Banbury mixer, a Henschel mixer, a rubber mill, an extruder mixer, or other equivalent device. The various ingredients which are used in conjunction with the polymer may be physically intimately blended therewith either in the absence of, or in the presence of, a common solvent; or, in a solvent which is capable of dissolving the polymer component of the composition and yet substantially incapable of dissolving the stabilizer ingredients. Typical of such solvents/dispersing agents include hexene or benzene. Subsequent to intimately dispersing the various components of the stabilized mixture within one another, the dispersing agent (if any) can be removed by selective evaporation and the resultant stabilized resin recovered. The resin may thereafter be formed into usable products by a variety of convenient methods.

The ultraviolet light stability of the composition prepared in the above fashion can be evaluated by exposing a sample thereof to Xenon or carbon arc light in a Weather-Ometer operated at a temperature of about 60° C. Degradation of the sample is monitored periodically by measuring the carbonyl absorption band at 1720 cm$^{-1}$ using an IR spectrophotometer. The relatively rapid formation of carbonyl sites indicates photodegradation of the sample. This procedure is a recognized method for evaluation of the efficacy of UV stabilizers and is described in the open literature, see of example, "Photodegradation, Photooxidation and Photostabilization of Polymers", by Ranby and Raybeck, John Wiley and Sons, New York City (1975) at pp. 125 et seq., and is also disclosed in U.S. Pat. No. 3,909,493. Photodegradation of the sample can also be manifested by cracking the sample upon heating it to about 180° C. Oxidative degradation and thermal degradation of the sample can be verified by monitoring the time required to effect discoloration and/or embrittlement of the sample in aging oven maintained at about 140° C.

EXAMPLES

The Examples which follow, further define, describe, and illustrate the preparation and evaluation of the polymer compositions prepared according to this invention. Apparatus and procedures used in both the preparation and evaluation of the compositions described herein are standard or as set forth hereinabove. Parts of percentages appearing in such examples are by weight unless otherwise stipulated.

EXAMPLE I

Preparation of
3,3,5,5,7-pentamethyl-1-(2,2,6,6-tetramethyl-4-piperidinyl)-1,4-diazocycloheptan-2-one In a 250 ml three-necked flask were placed 9.8 grams (0.038 mole) of 4-(3-amino-1,3-dimethylbutylamino)-2,2,6,6-tetramethylpiperidine, 9.2 grams chloroform, 10.6 grams acetone, and 0.33 gram of benzyltrimethylammonium chloride. The flask containing the above mixture was immersed in an ice bath and subjected to continuous agitation while 12.4 grams of 50% sodium hydroxide was introduced by dropwise addition. The pot temperature of the mixture was maintained below 25° during such addition. The reaction was allowed to proceed overnight with constant agitation. The following morning additional sodium hydroxide (12.4 grams of 50% aqueous solution) and chloroform (4.0 grams) were also added. Five hours after such addition, the reaction was worked up by adding 150 ml chloroform and 200 ml of water. The water layer was extracted twice with chloroform and combined with the original chloroform layer. The combined chloroform layer was washed three times with 150 ml of water. The chloroform layer was dried over anhydrous magnesium sulfate and concentrated to leave a yellow liquid. This yellow liquid was fractioned at reduced pressure. The fraction which boils at 130°-135° C. (0.95 mm Hg) is the desired product. Elemental analysis of this product confirms that it is the title compound.

EXAMPLE II

Preparation of
1-[4-(1-oxo-2,2,6,6-tetramethyl-piperidine)]-3,3-pentamethylene-5,5-dimethyl-4-oxo-piperazin-2-one 1.3 grams 1-[4-(2,2,6,6-tetramethyl-piperidine)]-3-3,3-pentamethylene-5,5-dimethyl-piperazine-2-one and 30 milliliters of chloroform were placed in a 250 milliliter flask. 32 grams m-chlorobenzoic acid were added to the flask in metered amounts over a period of 20 minutes. The reaction was stirred for 6 hours. Additional chloroform (20 milliliters) wash introduced into the flask after the six hour reaction interval and the mixture washed (2×) with 5% sodium carbonate solution. The product thus obtained was thereupon dried over sodium sulfate, concentrated and the solids recrystallized from hexane, mp 156°-158° C.

EXAMPLE III

Preparation of
1-[4-(2,2,6,6-tetramethyl-piperidine)]-3,3-pentamethylene-5,5-dimethyl-piperazine-2-one In a 100 milliliter three-necked flask, equipped with an air-stirrer, thermometer and addition funnel were placed 4.46 grams N'-[4(2,2,6,6-tetramethyl-piperidine)]-2-methyl-1, 2-propanediamine, 3.0 grams cyclohexanone cyanohydrin, 35 grams chloroform and 0.2 grams benzyltriethylammonium chloride. The flask was partially immersed in an ice bath and the contents thereof kept in a constant state of mild agitation. The reaction temperature was continuously monitored and maintained between 10° and 15° C. After 2 hours, 50 milliliters of chloroform was introduced into the flask together with sufficient water to dissolve the solids. Upon separation of the fluid contents into two distinct layers, the aqueous layer is extracted (2×) with 25 milliliters water, dried over sodium sulfate and concentrated. The desired product crystallized from solution upon standing and was recovered by filtration. Purification was effected in the conventional manner, mp 141°-143° C.

EXAMPLE IV

Preparation of 1-[4-(2,2,6,6-tetramethyl piperidine)]-3,5,5-trimethyl-3-hexyl-piperazine-2-one The procedures of Example III were repeated except for the substitution of 2-octanone for cyclohexanone cyanohydrin. The title compound thus obtained had a melting point of 88°-91.5° C.

EXAMPLE V

Preparation of 1-[4-(1,2,2,6,6-pentamethyl piperidine)]-3,3-pentamethylene-4,5,5-trimethyl piperazine-2-one The procedures of Example II were repeated except for the substitution of formic acid for m-chlorobenzoic acid. The title compound thus obtained had a melting point of 97°–99.5° C.

EXAMPLE VI

Preparation of 1-[4-(2,2,6,6-tetramethyl-piperidine)]-3,3,5,5-tetramethyl-piperazine-2-one The procedures of Example III were repeated except for the substitution of acetone cyanohydrin for cyclohexanone cyanohydrin. The title compound thus obtained had a melting point of 134°–6° C.

Each of the compounds of Examples I–VI was thereafter individually dry-blended with 100 grams of Hercules PROFAX 6501 polypropylene on a Fisher-Kendall mixer in a one-quart plstic screwcap jar. The weight of the stabilizer and polymer were adjusted for the desired concentration (0.25 phr). The compounded materials were thereupon extruded on a Brabender Plasticorder at 225° C. and pressed into 10 mm thick plaques (approximately 5×5 in. square) at 223° C. and 30,000 psi on a standard press. Control samples were also prepared in the above fashion, one sample containing no stabilizer and a second control stabilized 0.25 phr Tinuvin 327. In addition to the above ingredients, all samples tested contained 0.1 phr Goodrite 3125.

EVALUATION PROCEDURES

Oven aging a representative plaque was mounted through holes punched therein on a glass rod, each plaque being separated by a porcelain spacer and thereafter suspended in a draft oven at 140° C. The failure time was taken at the time when a portion of the plaque becomes brittle or burnt. Oftentimes the sample turns white and then brown in the degraded area.

Weather-Ometer aging a representative plaque of the above composition was mounted on an aluminum holder in an appropriate size to fit within an IR spectrophotometer. The plaque was then placed in a holder and inserted into an Xenon Weather-Ometer. At various time intervals, the samples were removed and the IR spectrum from 1910–1700 $cm^{-1}$ were recorded. The development of carbonyl sites at 1720 $cm^{-1}$ were also recorded. The development of carbonyl sites at 1720 $cm^{-1}$ relative to the reference peak at 1890 $cm^{-1}$ (carbonyl index) versus time is monitored. The failure time is the time necessary for the carbonyl absorbance to reach 0.05 or brittleness, whichever occurs first. The title compound evaluated according to the above procedures substantially enhanced the stability of the polypropylene to UV degradation in comparison to an unstabilized sample.

The results of the above evaluation are provided in the following table:

TABLE I

| Stabilizer (if any) | Failure Time (hrs) |
| --- | --- |
| None | 700 |
| Compound of Ex. I | 2230 |
| Compound of Ex. II | >2500 |
| Compound of Ex. III | >2500 |
| Compound of Ex. IV | >2500 |
| Compound of Ex. V | >2500 |

As is clearly demonstrated by the foregoing data, the stabilizer compounds described herein are highly effective in retarding photodegradation of polyolefins, e.g. polypropylene. The degree of protection afforded far surpasses commercially available materials such as Tinuvin 327 at equivalent concentrations. The foregoing Examples have been provided in aid of understanding the manner of making and utilizing the subject invention and are not intended as delineation of its scope which is set forth in the following claims.

We claim:

1. Compounds of the formula:

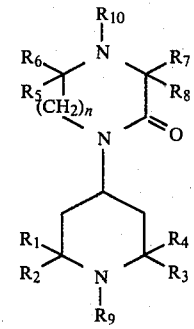

wherein $R_1$ through $R_4$ can be hydrogen or alkyl of 1 to 10 carbon atoms;

$R_5$ and $R_6$ are independently selected from the group consisting of alkyl of 1 to 12 carbon atoms, cycloalkyl, hydroxycycloalkyl, aminoalkyl, iminoalkyl, alkenyl, aralkyl and alkylene, provided further that any two of said substituents pendant from the same carbon atom can collectively form a cyclic or alicyclic hydrocarbon;

$R_7$ and $R_8$ are selected from the same group of substituents as $R_5$ and $R_6$ above;

$R_9$ and $R_{10}$ is oxygen, hydrogen or alkyl of 1 to 12 carbon atoms; and n is 1 to 3.

2. The compound of claim 1, 1-[4-(1-oxo-2,2,6,6-tetramethyl-piperidine)]-3,3-pentamethylene-5,5-dimethyl-4-oxo-piperazin-2-one.

3. The compound of claim 1, 1-[4-(2,2,6,6-tetramethyl-piperidine)]-3,3-pentamethylene-5,5-dimethylpiperazine-2-one.

4. The compound of claim 1, 1-[4-(2,2,6,6-tetramethyl piperidine)]-3,5,5-trimethyl-3-hexyl-piperazine-2one.

5. The compound of claim 1, 1-[4-(1,2,2,6,6-pentamethyl piperidine)]-3,3-pentamethylene-4,5,5-trimethyl piperazine-2-one.

6. The compound of claim 1, 1-[4-(2,2,6,6-tetramethyl-piperidine)]-3,3,5,5-tetramethyl-piperazine-2-one.

* * * * *